United States Patent [19]

Lesieur et al.

[11] Patent Number: 5,721,276
[45] Date of Patent: Feb. 24, 1998

[54] ARYLALKYL(THIO)CARBOXAMIDES

[75] Inventors: Isabelle Lesieur, Gondecourt; Patrick Depreux, Armentieres; Véronique Leclerc, Lille; Philippe Delagrange, Issy les Moulineaux; Pierre Renard, Versailles; Béatrice Guardiola Lemaitre, Saint Cloud, all of France

[73] Assignee: Adir et Compagnie, Courbevoie, France

[21] Appl. No.: 657,972

[22] Filed: May 30, 1996

[30] Foreign Application Priority Data

May 31, 1995 [FR] France ................... 95 06435

[51] Int. Cl.⁶ .................. A61K 31/165; C07C 233/05
[52] U.S. Cl. ............... 514/617; 514/419; 514/443; 514/469; 514/595; 514/599; 548/490; 548/491; 549/51; 549/58; 549/467; 564/74; 564/170; 564/171; 564/172
[58] Field of Search .................. 564/215, 217, 564/218, 219, 74, 170, 171, 172; 514/629, 630, 599, 595, 443, 469, 419, 617; 549/58, 51, 467; 548/490, 491

[56] References Cited

U.S. PATENT DOCUMENTS 5,194,614  3/1993  Andrieux et al. ............ 544/400
5,591,775  1/1997  Depreux et al. ............ 514/580

*Primary Examiner*—Shailendra Kumar
*Attorney, Agent, or Firm*—The Firm of Gordon W. Hueschen

[57] ABSTRACT

The invention relates to a compound selected from those of formula (I):

$$A-B-\underset{\underset{X}{\|}}{C}-NH-R_1 \qquad (I)$$

in which A, B, X and $R_1$ are as defined in the description, and medicinal product containing the same useful for treating a disorder of the melatoninergic system.

10 Claims, No Drawings

ARYLALKYL(THIO)CARBOXAMIDES

The invention relates to new arylalkyl(thio)carboxamide compounds, to the processes for their preparation and to the pharmaceutical compositions containing them.

The invention describes new arylalkyl(thio)carboxamide compounds which have proved to be potent ligands of the melatoninergic receptors.

There are known in the prior art (3-indolyl)alkyl(thio) amide compounds which are used as intermediates for the synthesis of heterocyclic thioisomunchnone compounds (Padwa A. et al. Synthesis 1994, No. 9, pp 993–1004) or as products of the Ritter reaction (Kost A. N. et al. Vest. Mosk. Univ. Khim., 1975, 16, pp 22–6).

There are also known N-methyl-3-(4-methoxy-1-naphthyl)propionamide and N-tert-butyl-3-carboxy-4-(1-naphthyl)butyramide which are useful as synthesis intermediates for preparing respectively a benzocyclohexanedione lactone (Taylor E. C. et al. J. Am. Chem. Soc., 1981, 103, pp 6856–6863) and a renin inhibitor (EP 427939) as well as a 2-naphthylacetamide compound which is useful for the preparation of hydroxamic acid compounds (Hoffman R. V. et al. J. Org. Chem., 1992, 57, pp 5700–5707).

Numerous studies have demonstrated over the past ten years the vital role of melatonin (N-acetyl-5-methoxytryptamine) in the control of the circadian rhythm and of the endocrine functions, and the melatonin receptors have been characterized and localized.

In addition to their beneficial action on circadian rhythm disorders (J. Neurosurg 1985, 63, pp 321–341) and sleep disorders (Psychopharmacology, 1990, 100, pp 222–226), the ligands of the melatoninergic system possess advantageous pharmacological properties on the central nervous system, especially anxiolytic and antipsychotic properties (Neuropharmacology of Pineal Secretions, 1990, 8 (3–4), pp 264–272) and analgesic properties (Pharmacopsychiat., 1987, 20, pp 222–223) as well as for the treatment of Parkinson's disease (J. Neurosurg 1985, 63, pp 321–341) and Alzheimer's disease (Brain Research, 1990, 528, pp 170–174). Likewise, these compounds have shown an activity on some cancers (Melatonin—clinical Perspectives, Oxford University Press, 1988, page 164–165), on ovulation (Science 1987, 227, pp 714–720), and on diabetes (Clinical endocrinology, 1986, 24, pp 359–364).

Compounds which make it possible to act on the melatoninergic system are therefore, for the clinician, excellent medicinal products for the treatment of pathologies linked to disorders of the melatoninergic system, especially those mentioned above.

The invention relates to the compounds of formula (I):

in which:

A represents a group of formula:

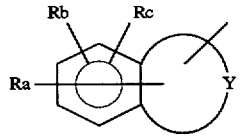

in which:

Y forms with the benzo nucleus carrying it a ring chosen from naphthalene, dihydronaphthalene, tetrahydronaphthalene, benzofuran, 2,3-dihydrobenzofuran, benzothiophene, 2,3-dihydrobenzothiophene, indole, indoline, 2H-indene and indan;

Ra, Rb and Rc, each independently of each other, represent a hydrogen atom or a radical chosen from a halogen atom, hydroxy, —Rd and —O—Rd; with Rd being chosen from alkyl, alkyl substituted with one or more halogen atoms, alkenyl, alkynyl, cycloalkyl, cycloalkylalkyl, aryl, arylalkyl, substituted aryl, substituted arylalkyl; it also being possible for Ra to form with Rb and the 2 adjacent carbon atoms carrying them a ring $A_1$ chosen from furan, dihydrofuran, pyran and dihydropyran, $A_1$ being optionally substituted by one or more radicals or groups chosen from hydroxy, alkyl, alkoxy and oxo;

B represents an alkylene chain having 2 to 6 carbon atoms, unsubstituted or substituted with one or more radicals chosen from alkyl, alkoxy, hydroxy, carboxy, alkoxycarbonyl, carboxyalkyl and alkoxycarbonylalkyl, it being understood that B may also represent a methylene chain when Y forms with the benzo nucleus carrying it a naphthalene, a dihydronaphthalene or a tetrahydronaphthalene and that Ra, Rb and Rc do not simultaneously represent hydrogen atoms;

with the proviso that Ra, Rb and Rc cannot simultaneously represent hydrogen atoms or one hydrogen atom and 2 methyl radicals or 2 hydrogen atoms and one methyl radical when Y forms, with the benzo nucleus to which it is attached, an indole, and that the compound of formula (I) cannot be N-methyl-3-(4-methoxy-1-naphthyl)propionamide or N-tert-butyl-3-carboxy-4-(1-naphthyl)butyramide, X represents an oxygen or a sulfur atom;

and $R_1$ represents a radical chosen from alkyl, alkyl substituted with one or more halogen atoms, alkenyl, alkynyl, cycloalkyl and cycloalkylalkyl, it being understood that:

the terms "alkyl" and "alkoxy" designate linear or branched groups containing from 1 to 6 carbon atoms, the terms "alkenyl" and "alkynyl" designate linear or branched unsaturated groups containing from 2 to 6 carbon atoms, the term "cycloalkyl" designates a group having 3 to 8 carbon atoms, the term "aryl" designates a phenyl, naphthyl or pyridyl radical, the term "substituted" applied to the expressions "aryl" and "arylalkyl" means that these groups may be substituted with one or more radicals chosen from a halogen atom, alkyl, alkoxy, hydroxy and alkyl substituted with one or more halogen atoms;

to their enantiomers and diastereoisomers, and to their addition salts with a pharmaceutically acceptable acid or base, The invention relates more particularly to the compounds of formula (I) in which, taken separately or together:

A represents a naphthyl,

A represents a substituted naphthyl,

A represents a partially hydrogenated naphthyl, for example a substituted 1,2-dihydronaphthyl or a substituted 1,2,3,4-tetrahydronaphthyl, A represents a partially hydrogenated substituted naphthyl, for example a substituted 1,2- dihydronaphthyl or a substituted 1,2,3,4-tetrahydronaphthyl,

A represents a benzofuryl,

A represents a substituted benzofuryl,

A represents a benzothienyl,

A represents a substituted benzothienyl.

A represents an indolyl,

A represents a substituted indolyl,

A is substituted with an alkoxy radical,

A is substituted with a halogen atom,

A is substituted with an alkyl,

B represents a methylene chain,

B represents an ethylene chain,

B represents a chain —(CH$_2$)$_3$—,

X represents a sulfur atom,

X represents an oxygen atom,

R$_1$ represents an alkyl,

R$_1$ represents an alkyl substituted with one or more halogen atoms,

R$_1$ represents a cycloalkyl, and R$_1$ represents a cycloalkylalkyl.

For example, the invention relates to the specific compounds of formula (I) corresponding to the following formulae (1) to (12):

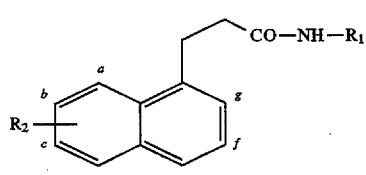 (1)

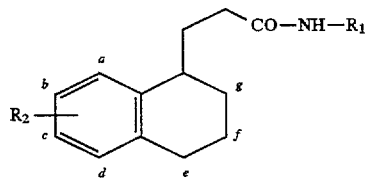 (2)

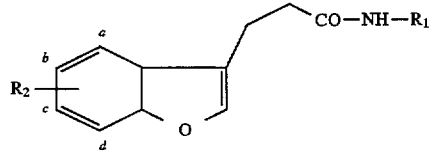 (3)

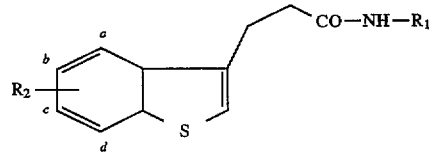 (4)

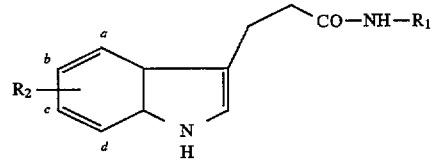 (5)

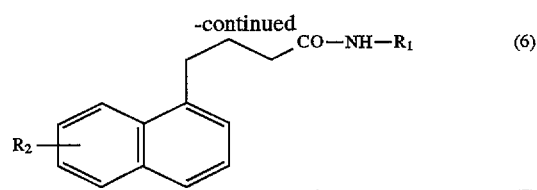 (6)

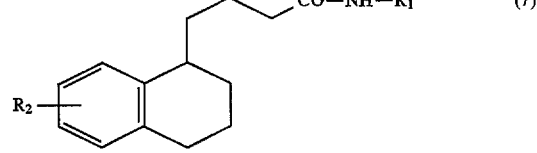 (7)

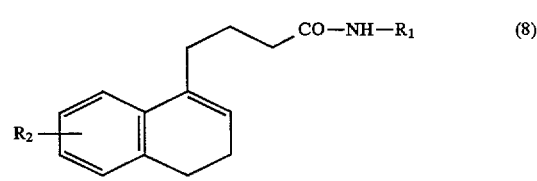 (8)

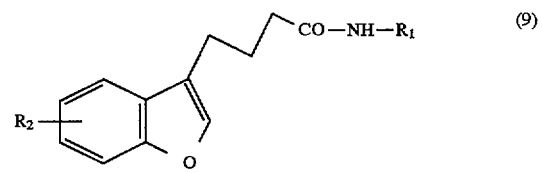 (9)

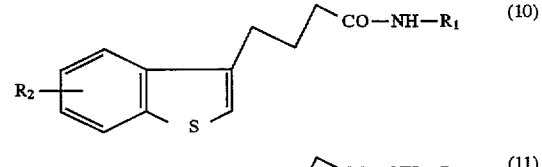 (10)

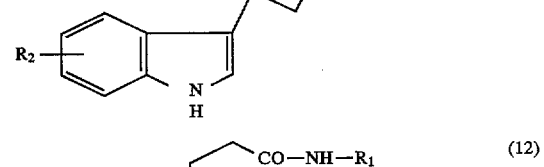 (11)

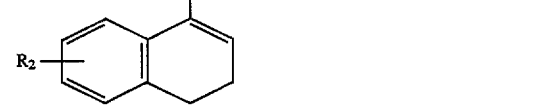 (12)

in which R$_2$ represents a radical chosen from the halogen atom, hydroxy, —Rd and —O—Rd with Rd as defined in the formula (I).

For example R$_2$ represents a radical chosen from a halogen atom, alkyl and alkoxy.

The invention relates more particularly to the compounds of formula (I) in which the radical R$_2$ is at the b position of the naphthyl or of the tetrahydronaphthyl and the compounds of formula (I) in which R$_2$ is at the b position of the benzofuryl, benzothiophene or indolyl ring.

In particular, the alkyl radicals present in the formula (I) may be chosen from methyl, ethyl, n-propyl, isopropyl, n-butyl, isobutyl, sec-butyl, tert-butyl, pentyl and hexyl and the structural isomers for the pentyl and hexyl radicals, the alkoxy radicals present in the formula (I) may be chosen from methoxy, ethoxy, n-propoxy, isopropoxy, n-butoxy, isobutoxy, sec-butoxy, tert-butoxy, pentyloxy and hexyloxy and the structural isomers of the pentyloxy and hexyloxy radicals, the halogen atoms present in the formula (I) may be chosen from bromine, chlorine, fluorine and iodine, the cycloalkyls present in the formula (I) may be chosen from cyclopropyl, cyclobutyl, cyclopentyl, cyclohexyl, cycloheptyl and cyclooctyl, and the alkylene groups present in the formula (I) may be chosen from methylene, ethylene, trimethylene, tetramethylene, pentamethylene and hexamethylene.

Among the pharmaceutically acceptable acids which may be used to form an addition salt with the compounds of the invention, there may be mentioned, by way of examples and with no limitation being implied, hydrochloric, sulfuric, phosphoric, tartaric, malic, maleic, fumaric, oxalic, methanesulfonic, ethanesulfonic, camphoric and citric acids.

Among the pharmaceutically acceptable bases which may be used to form an addition salt with the compounds of the invention, there may be mentioned by way of examples and with no limitation being implied sodium, potassium, calcium or aluminum hydroxides, alkali or alkaline-earth metal carbonates, and organic bases such as triethylamine, benzylamine, diethanolamine, tert-butylamine, dicyclohexylamine and arginine.

The invention also relates to a process for the preparation of the compounds of formula (I), wherein an acid of formula (II):

A—B—COOH     (II)

in which A and B are as defined in the formula (I), is reacted with an amine of formula (III):

H$_2$N—R$_1$     (III)

in which R$_1$ is as defined in the formula (I), in order to obtain the compound of formula (I/a):

A—B—C—NH—R$_1$     (I/a)
∥
O in which A, B and R$_1$ are as defined above, which compound of formula (I/a), when treated with a thionation reagent, for example the Lawesson's reagent, gives the compound of formula (I/b):

A—B—C—NH—R$_1$     (I/b)
∥
S in which A, B and R$_1$ are as defined above, the compounds of formula (I/a) and (I/b) forming the set of compounds of formula (I) which may, if desired, be purified according to one or more purification methods chosen from crystallization, chromatography, extraction, filtration and passage over charcoal or a resin, separated, where appropriate, in a pure form or in the form of a mixture, into their possible enantiomers or diastereoisomers, and/or salified by a pharmaceutically acceptable acid or base.

The invention also relates to the process for the preparation of compounds of formula (I/c), a specific case of the compounds of formula (I):

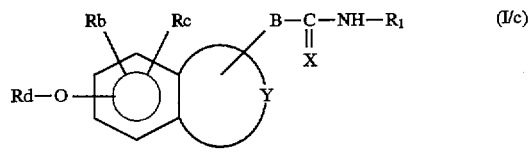

in which B, X, Y, R$_1$, R$_b$, R$_c$ and R$_d$ are as defined in the formula (I), wherein the radical R$_d$ is grafted onto a compound of formula (I/d):

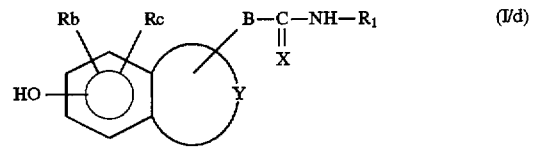

in which B, X, Y, R$_1$, R$_b$ and R$_c$ are as defined above, which compounds of formula (I/c) may, if desired, be purified according to one or more purification methods chosen from crystallization, chromatography, extraction, filtration and passage over charcoal or a resin, separated, where appropriate, in a pure form or in the form of a mixture, into their possible enantiomers or diastereoisomers, and/or salified by a pharmaceutically acceptable acid or base.

The grafting of the radical R$_d$ may, for example, be performed by means of a compound of formula (IV):

Rd—W     (IV)

in which R$_d$ is as defined in the formula (I) and W represents a halogen atom or a leaving group.

The compounds of formula (I/d):

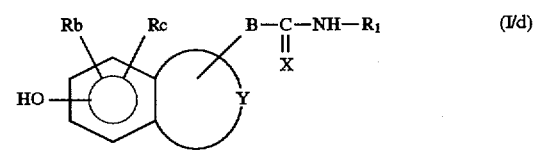

in which B, X, Y, R$_1$, R$_b$ and R$_c$ are as defined in the formula (I) are accessible to persons skilled in the art by dealkylation of a compound of formula (I/e):

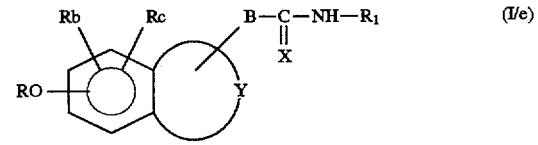

in which B, X, Y, R$_1$, R$_b$ and R$_c$ are as defined above and R represents a (C$_1$–C$_6$)alkyl, for example a methyl.

For example, the dealkylation of the compound of formula (I/e) may be performed using BBr$_3$ or a mixture AlX'$_3$, R'—SH in which X' is a halogen atom and R' is a (C$_1$–C$_6$) alkyl.

The invention also relates to the process for the preparation of the compounds of formula (I/f):

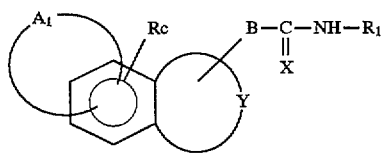

(I/f)

in which B, X, Y, R₁, Rc and A₁ are as defined in the formula (I) by cyclization of a compound of formula (I/g):

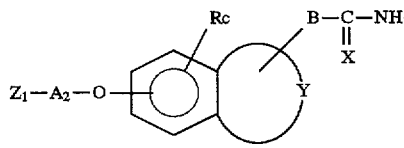

(I/g)

in which B, X, Y, R₁ and Rc are as defined above, A₂ represents a chain chosen from $(C_2-C_3)$ alkylene and $(C_2-C_3)$ alkenylene, A₂ being unsubstituted or substituted with one or more groups chosen from hydroxy, alkyl, alkoxy and oxo, and Z₁ being a reactive functional group, which compounds of formula (I/f) may, if desired, be purified according to one or more purification methods chosen from crystallization, chromatography, extraction, filtration and passage over charcoal or a resin, separated, where appropriate, in a pure form or in the form of a mixture, into their possible enantiomers or diastereoisomers, and/or salified by a pharmaceutically acceptable acid or base.

The invention also relates to the process for the preparation of a compound of formula (I/h):

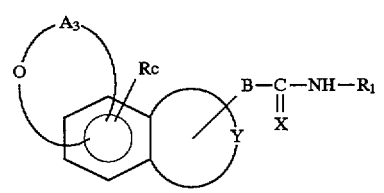

(I/h)

in which B, X, Y, R₁, and Rc are as defined in the formula (I) and A₃ represents a $(C_2-C_3)$ alkylene chain which is unsubstituted or substituted with a $(C_1-C_6)$ alkyl radical, wherein a compound of formula (I/i):

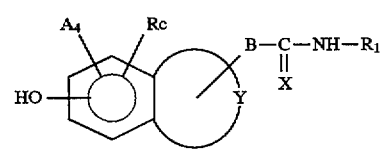

(I/i)

in which B, X, Y, R₁, and Rc are as defined above and A₄ represents a $(C_2-C_3)$ alkenyl radical which is unsubstituted or substituted with a $(C_1-C_6)$ alkyl radical, is cyclized, which compounds of formula (I/h) may, if desired, be purified according to one or more purification methods chosen from crystallization, chromatography, extraction, filtration and passage over charcoal or a resin, separated, where appropriate, in a pure form or in the form of a mixture, into their possible enantiomers or diastereoisomers, and/or salified by a pharmaceutically acceptable acid or base.

The invention also relates to the process for the preparation of the compounds of formula (I/j):

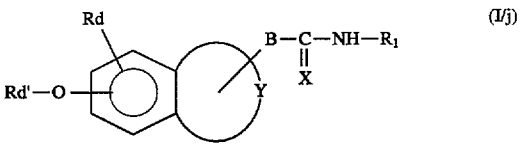

(I/j)

in which Rd, Y, X, B and R₁ are as defined in the formula (I) and Rd' may take the same values as Rd as defined above, wherein the radical Rd as defined above is grafted onto the hydroxy functional group of a compound of formula (I/k):

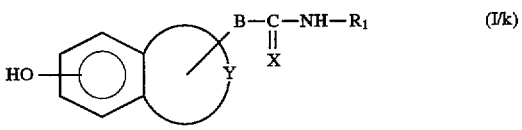

(I/k)

in which Y, B, X and R₁ are as defined above, in order to obtain a compound of formula (I/l):

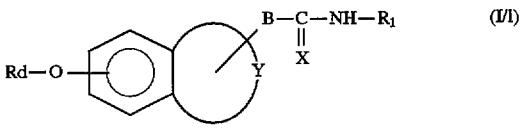

(I/l)

in which Rd, Y, B, X and R₁ are as defined above, which compound of formula (I/l) is then subjected to a transposition reaction in order to obtain the compound of formula (I/m):

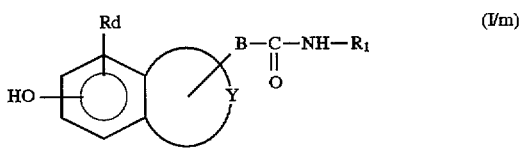

(I/m)

in which Rd, Y, B, X and R₁ are as defined above, the hydroxy functional group again being grafted with a radical Rd, as defined above, in order to obtain a compound of formula (I/j):

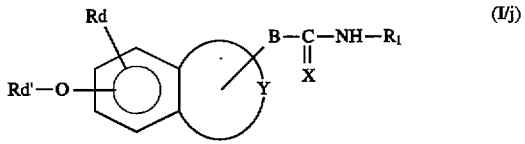

(I/j)

in which Rd, Rd', Y, B, X and R₁ are as defined above, which compounds of formula (I/j) may, if desired, be purified according to one or more purification methods chosen from crystallization, chromatography, extraction, filtration and passage over charcoal or a resin, separated, where appropriate, in a pure form or in the form of a mixture, into their possible enantiomers or diastereoisomers, and/or salified by a pharmaceutically acceptable acid or base.

The compounds of formula (I) possess very advantageous pharmacological properties for the clinician.

The compounds of the invention and the pharmaceutical compositions containing them have proved to be useful for the treatment of disorders of the melatoninergic system and of disorders linked to the melatoninergic system.

Pharmacological studies of the derivatives of the invention have indeed shown that they are not toxic, are endowed with a very high selective affinity for the melatonin receptors and possess substantial activities on the central nervous system and in particular, which make it possible to establish that the compounds of the invention are useful in the treatment of stress, of sleep disorders, anxiety, seasonal depressions, cardiovascular pathologies, insomnia and fatigue due to jetlag, schizophrenia, panic attacks, melancholy, appetite disorders, obesity, psoriasis, psychotic disorders, epilepsy, Parkinson's disease, senile dementia, various disorders linked to normal or pathological aging, migraine, memory loss, Alzheimer's disease, as well as cerebral circulation disorders. In another field of activity, it appears that the products of the invention possess ovulation-inhibiting properties and immunomodulatory properties and that they are capable of being used in anticancer treatment.

The compounds will preferably be used in the treatment of seasonal depressions, sleep disorders, cardiovascular pathologies, insomnia and fatigue due to jetlag, appetite disorders and obesity.

For example, the compounds will be used in the treatment of seasonal depressions and of sleep disorders.

The subject of the present invention is also the pharmaceutical compositions containing a compound of formula (I) in combination with one or more pharmaceutically acceptable excipients.

Among the pharmaceutical compositions according to the invention, there may be mentioned, more particularly, those which are suitable for oral, parenteral, nasal, per. or transcutaneous, rectal, perlingual, ocular or respiratory administration, especially plain or sugar-coated tablets, sublingual tablets, sachets, packets, hard gelatine capsules, glossettes, lozenges, suppositories, creams, ointments, skin gels, and oral or injectable ampoules.

The dosage varies according to the sex, age and weight of the patient, the route of administration, the nature of the therapeutic indication, or of the possible associated treatments and is between 0.1 mg and 1 g per 24 hours in 1 or 2 doses, more particularly between 1 and 100 mg, for example between 1 and 10 mg.

The following examples illustrate the invention, but do not limit it in any manner.

PREPARATION 1

3-(7-Methoxy-1-Naphthyl)Propanoic Acid

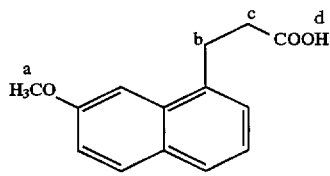

Reagents:
3-(7-methoxy-1-naphthyl)propionitrile: 1 g ($4.7\times10^{-3}$ mol)
Aqueous sodium hydroxide solution, 6N: 10 cm$^3$ ($6\times10^{-2}$ mol)
Methanol: 10 cm$^3$ Procedure:
The 3-(7-methoxy-1-naphthyl)propionitrile is dissolved in 10 cm$^3$ of methanol in a 100 cm$^3$ flask. The aqueous sodium hydroxide solution is added and the medium is heated at reflux overnight. The medium is allowed to cool and it is acidified with 6N aqueous HCl solution and then the precipitate formed is filtered off. It is recrystallized.

Characteristics:
Molar mass: 230.26 g.mol$^{-1}$ for $C_{14}H_{14}O_3$
Appearance: white solid
Melting point 154°–155° C.
Rf=0.40
Eluent: Acetone/toluene/cyclohexane (hereinafter ATC) (4/4/2)
Yield: 90%
Recrystallization solvent: toluene Infrared spectroscopy analysis:
1700 cm$^{-1}$: $\upsilon$CO acid
1620 and 1600 cm$^{-1}$: $\upsilon$C=C
1260 cm$^{-1}$: $\upsilon$CH$_3$O NMR spectroscopy analysis (80 MHz, DMSO, δ):
2.65 ppm (triplet, 2H): H$_b$ J$_{b-c}$=7.60 Hz
3.30 ppm (triplet, 2H): H$_c$ Jc-b=7.60 Hz
3.90 ppm (singlet, 3H): H$_a$
7.10–7.40 ppm (unresolved complex, 4H): H2,3,6,8
7.60–7.95 ppm (unresolved complex, 2H): H4,5
12,20 ppm (signal, 1H): Exchangeable H$_d$ in D$_2$O

PREPARATION 2

4-(7-Methoxy-1-Naphthyl)Butyric Acid

Stage A: Methyl 3-(7-Methoxy-1-Naphthyl) Propanoate

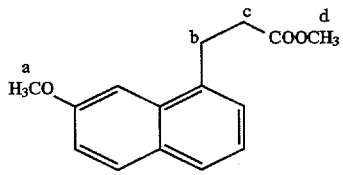

Reagents:
3-(7-Methoxy-1-naphthyl)propanoic acid: 0.2 g (0.9× 10$^{-3}$ mol)
Thionyl chloride: 0.25 cm$^3$ ($3.5\times10^{-3}$ mol)
Methanol: 20 cm$^3$ Procedure:
The acid is dissolved in methanol in a 100 cm$^3$ flask placed in an ice bath at −5° C. The thionyl chloride is added dropwise and the mixture is kept stirring for 1 h. It is evaporated and the residue is taken up in 10 cm$^3$ of ether. The organic phase is washed with a 10% aqueous potassium carbonate solution and with water. It is dried over CaCl$_2$, filtered and evaporated off.

Characteristics:
Molar mass: 244.29 g.mol$^{-1}$ for $C_{15}H_{16}O_3$
Appearance: oil
Rf=0.67
Eluent: ATC (4/4/2)
Yield: 89%

Infrared spectroscopy analysis:
3020–2800 cm$^{-1}$: $\upsilon$CH
1730 cm$^{-1}$: $\upsilon$CO ester 1620 and 1590 cm$^{-1}$: υC═C 1250 cm$^{-1}$: υCH$_3$O NMR spectroscopy analysis (300 MHz,CDCl$_3$, δ):

2.75 ppm (triplet, 2H): H$_b$ J$_{b-c}$=7.95 Hz 3.34 ppm (triplet, 2H): H$_c$ J$_{c-b}$=7.95 Hz 3.68 ppm (singlet, 3H): H$_d$ 3.90 ppm (singlet, 3H): H$_a$ 7.13–7.30 ppm (unresolved complex, 4H): H$_{2,3,6,8}$ 7.63 ppm (doublet, 1H): H$_4$ J$_{ortho}$=7.77 Hz 7.73 ppm (doublet, 1H): H$_5$ J$_{ortho}$=8.95 Hz

Stage B: 3-(7-Methoxy-1-Naphthyl)-1-Propanol

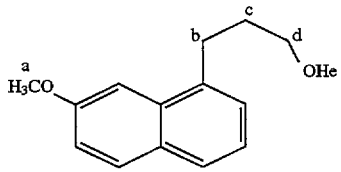

Reagents:

Methyl 3-(7-methoxy-1-naphthyl)propanoate: 0.5 g (2×10$^{-3}$ mol)

LiAlH$_4$: 0.3 g (8×10$^{-3}$ mol)

Anhydrous ether: 10 cm$^3$

Procedure:

LiAlH$_4$ and the ether are introduced into a 50 cm$^3$ flask placed in an ice bath at −5° C., and then the ester, previously diluted in ether, is added dropwise. The mixture is kept stirring for 1 h and it is hydrolyzed by pouring it over ice cold water. The medium is filtered and extracted with ether. The organic phase is dried, filtered and evaporated off.

Characteristics:

Molar mass: 217.29 g.mol$^{-1}$ for C$_{14}$H$_{16}$O$_2$

Appearance: white solid

Melting point: 38°–39° C.

Rf: 0.13

Eluent: chloroform

Yield: 88%

Recrystallization solvent: cyclohexane

Infrared spectroscopy analysis:

3300 cm$^{-1}$: υOH broad band

3040–2800 cm$^{-1}$: υCH 1620 and 1590 cm$^{-1}$: υC═C 1250 cm$^{-1}$: υCH$_3$O

NMR spectroscopy analysis (300 MHz,CDCl$_3$, δ):

2.00–2.10 ppm (multiplet, 2H): H$_c$ 3.15 ppm (triplet, 2H): H$_b$ J$_{b-c}$=7.59 Hz 3.75 ppm (triplet, 2H): H$_d$ J$_{d-c}$=6.24 Hz 3.95 ppm (singlet, 3H): H$_a$ 7.13–7.37 ppm (unresolved complex, 4H): H$_{2,3,6,8}$ 7.66 ppm (doublet, 1H): H$_4$ J$_{ortho}$=7.83 Hz 7.76 ppm (doublet, 1H): H$_5$ J$_{ortho}$=8.92 Hz

Stage C: 3-(7-Methoxy-1-Naphthyl)-1-Propanol Mesylate

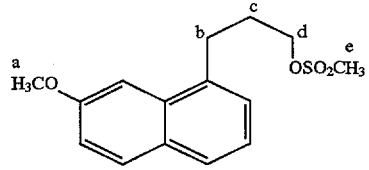

Reagents:

3-(7-methoxy-1-naphthyl)propanol: 5.1 g (23.5×10$^{-3}$ mol)

CH$_3$SO$_2$Cl: 3.3 g (28.2×10$^{-3}$ mol)

NEt$_3$: 3.9 cm$^3$ (28.2×10$^{-3}$ mol)

CH$_2$Cl$_2$: 100 cm$^3$

Procedure:

The 3-(7-methoxy-1-naphthyl)propanol is dissolved in the CH$_2$Cl$_2$ in a 250 cm$^3$ round-bottomed flask. The triethylamine is added. The round-bottomed flask is placed in an ice and salt bath (−5° C.). The mesyl chloride is added dropwise. The mixture is kept stirring for 2 h. The organic phase is washed with 3×20 cm$^3$ HCl and then with water until the waters become neutral. It is dried over CaCl$_2$, filtered and evaporated off. The solid obtained is recrystallized.

Characteristics:

Molar mass: 294.37 g.mol$^{-1}$ for C$_{15}$H$_{18}$O$_4$S

Melting point: 52°–54° C.

Rf: 0.71

Eluent: CHCl$_3$/MeOH (19/1)

Yield: 71%

Recrystallization solvent: toluene/cyclohexane (1/3)

Infrared spectroscopy analysis:

3040–2820 cm$^{-1}$: υCH alkyls 1610 and 1590 cm$^{-1}$: υC═C 1330 cm$^{-1}$: υSO$_2$ asym 1260 cm$^{-1}$: υOCH$_3$ 1170 cm$^{-1}$: υSO$_2$ sym NMR spectroscopy analysis (300 MHz, DMSO, δ)

2.08 ppm (multiplet, 2H): H$_c$ 3.12 ppm (triplet, 2H): H$_b$ J$_{b-c}$=7.75 Hz 3.22 ppm (singlet, 3H): H$_e$ 3.92 ppm (singlet, 3H): H$_a$ 4.32 ppm (triplet, 2H): H$_d$ J$_{d-c}$=6.20 Hz 7.19 ppm (split doublet, 1H): H$_6$ J$_{ortho}$=8.93 Hz, J$_{meta}$=2.38 Hz 7.26–7.37 ppm (unresolved complex, 3H): H$_{2,3,8}$ 7.72 ppm (doublet, 1H): H$_4$ J$_{ortho}$=7.88 Hz 7.85 ppm (doublet, 1H): H$_5$ J$_{ortho}$=8.93 Hz

Stage D: [4-(7-Methoxy-1-Naphthyl)Butyronitrile

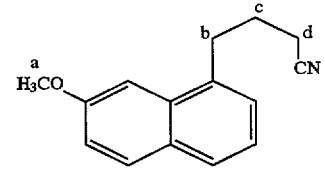

Reagents:

3-(7-methoxy-1-naphthyl)-1-propanol mesylate: 3 g (10.2×10$^{-3}$ mol)

KCN: 2 g (30.6×10$^{-3}$ mol)

DMSO: 20 cm$^3$

Procedure:

The 3-(7-methoxy-1-naphthyl)-1-propanol mesylate is dissolved in the DMSO in a 100 cm$^3$ flask. KCN is added and the mixture is refluxed for 2 h. It is allowed to cool. It is poured into a water/ice mixture. It is extracted with ether. The organic phase is washed with water, dried over CaCl$_2$ and evaporated off. The product obtained is recrystallized.

Characteristics:

Molar mass: 225.29 g.mol$^{-1}$ for C$_{15}$H$_{15}$NO

Melting point: 52°–54° C.

Rf: 0.39

Eluent: ATC (2/3/5)

Yield: 90%

Recrystallization solvent: alcohol/water (1/5)

Infrared spectroscopy analysis:

3040–2820 cm$^{-1}$: νCH alkyls 2240 cm$^{-1}$: νCN 1620 and 1590 cm$^{-1}$: νC=C 1250 cm$^{-1}$: νOCH$_3$ NMR spectroscopy analysis (300 MHz, CDCl$_3$, δ)

2.09 ppm (multiplet, 2H): H$_c$ 2.35 ppm (triplet, 2H): H$_d$ J$_{d-c}$=6.87 Hz 3.18 ppm (triplet, 2H): H$_b$ J$_{b-c}$=7.44 Hz 3.94 ppm (singlet, 3H): H$_a$ 7.16 ppm (split doublet, 1H): H$_6$ J$_{ortho}$=8.91 Hz, J$_{meta}$=2.44 Hz 7.23–7.30 ppm (unresolved complex, 3H): H$_{2,3,8}$ 7.67 ppm (split doublet, 1H): H$_4$ J$_{ortho}$=7.31 Hz, J$_{meta}$=1.77 Hz 7.76 ppm (doublet, 1H): H$_5$ J$_{ortho}$=8.91 Hz Stage E: 4-(7-Methoxy-1-Naphthyl)Butyric Acid

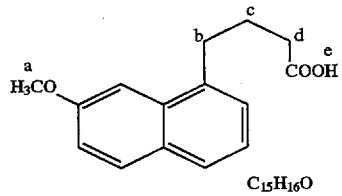

C$_{15}$H$_{16}$O

Reagents:

4-(7-Methoxy-1-naphthyl)butyronitrile: 1.8 g (8×10$^{-3}$ mol)

NaOH 10%: 3.5 cm$^3$ (8×10$^{-2}$ mol)

Methanol: 35 cm$^3$

HCl 1N

Procedure:

The nitrile is dissolved in the methanol in a 100 cm$^3$ flask. The sodium hydroxide is added. The mixture is refluxed for 16 h. It is allowed to cool and it is acidified with 1N HCl. The product obtained is filtered and recrystallized.

Characteristics:

Molar mass: 244.29 g.mol$^{-1}$ for C$_{15}$H$_{16}$O$_3$

Melting point: 104°–106° C.

Rf: 0.54

Eluent: ATC (4/4/2)

Yield: 94%

Recrystallization solvent: toluene/cyclohexane (1/4)

Infrared spectroscopy analysis:

3000–2860 cm$^{-1}$: νCH alkyl 1700 cm$^{-1}$: νCO acid 1620 and 1590 cm$^{-1}$: νC=C 1240 cm$^{-1}$: νOCH$_3$ NMR spectroscopy analysis (300 MHz, CDCl$_3$, δ):

2.11 ppm (multiplet, 2H): H$_c$ 2.51 ppm (triplet, 2H): H$_d$ J$_{d-c}$=6.98 Hz 3.09 ppm (triplet, 2H): H$_b$ J$_{b-c}$=7.84 Hz 3.95 ppm (singlet, 3H): H$_a$ 7.15 ppm (split doublet, 1H): H$_6$ J$_{ortho}$=8.94 Hz, J$_{meta}$=2.36 Hz 7.23–7.39 ppm (unresolved complex, 3H): H$_{2,3,8}$ 7.66 ppm (split doublet, 1H): H$_4$ J$_{ortho}$=7.44 Hz, J$_{meta}$=1.65 Hz 7.76 ppm (doublet, 1H): H$_5$ J$_{ortho}$=8.94 Hz, acidic H invisible in CDCl$_3$

PREPARATION 3

4-(5-Fluoro-3-Indolyl)Butyric Acid (J. Med. Chem. 1992, 35(22), pp 4020–4026)

PREPARATION 4

3-(5-Methyl-3-Benzothiophenyl)Propanoic Acid (Monatsh. Chem. 1968, 99(2), pp 715–720)

PREPARATION 5

3-(5-Benzyloxy-3-Benzothiophenyl)Propanoic Acid (J. Pharm. Pharmacol. 1973, 25(10), pp 847–848)

PREPARATION 6

3-(5-Propyl-3-Indolyl)Propanoic Acid

PREPARATION 7

3-(5-Trifluoromethyl-3-Indolyl)Propanoic Acid (J. Amer. Chem. Soc. 1970, 92(10), pp en)

PREPARATION 8

3-(6-Methoxy-3-Benzofuryl)Propanoic Acid (C. R. Acad-Sci. Ser. C, 1970, 270(11), pp 1027–1029)

PREPARATION 9

4-(5-Methoxy-3-Benzofuryl)Butyric Acid (Bull. Chem. Soc. Jpn 1976, 49(3), pp 737–740)

PREPARATION 10

4-(6-Methoxy-3-Indolyl)Butyric Acid (J. Chem. Soc., Chem. Commun., 1972, (8), pp 461–462)

PREPARATION 11

3-(5-Ethoxy-3-Indolyl)Propanoic Acid (J. Karnatak Univ. 1972, 17, pp 33–42)

PREPARATION 12

4-(4,6-Dimethoxy-3-Indolyl)Butyric Acid (J. Chem. Soc., Perkin Trans. 2, 1978, (8), pp 733–742)

PREPARATION 13

3-(5-Hydroxy-3-Benzofuryl)Propanoic Acid (Bull. Chem. Soc. Jpn 1982, 55(3), pp 865–869)

EXAMPLE 1

N-Methyl-2-(7-Methoxy-1-Naphthyl)Acetamide

Example 1

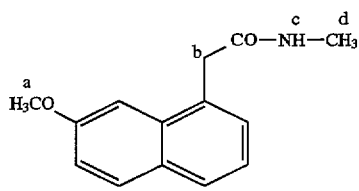

Reagents:

(7-Methoxy-1-naphthyl)acetic acid: 2 g ($9.3 \times 10^{-3}$ mol)

$SOCl_2$: 6.75 cm$^3$ ($93 \times 10^{-3}$ mol)

$NH_2CH_3$: 3.18 cm$^3$ ($37.2 \times 10^{-3}$ mol)

Procedure:

The acid and the thionyl chloride are heated at reflux for 1 h. The excess $SOCl_2$ is evaporated off. The residue is taken up in anhydrous $CHCl_3$. The medium is placed in an ice bath and the amine is added dropwise. The mixture is kept stirring for 2 h. The organic phase is extracted with water, 10% $K_2CO_3$, water and 6N hydrochloric acid and then water. It is dried over $CaCl_2$ and evaporated off. The residue is recrystallized.

Characteristics:

Molar mass: 229.28 g.mol$^{-1}$ for $C_{14}H_{15}NO_2$

Appearance: white solid

Melting point: 192°–193° C.

Rf: 0.48

Eluent: ATC (4/4/2)

Yield: 33%

Recrystallization solvent: toluene

Infrared spectroscopy analysis:

3280–3060 cm$^{-1}$: νNH amide

2920–2820 cm$^{-1}$: νCH 1640 cm$^{-1}$: νCO amide 1600 and 1590 cm$^{-1}$: νC═C 1260 cm$^{-1}$: νOCH$_3$ NMR spectroscopy analysis (300 MHz, CDCl$_3$, δ):

2.74 ppm (doublet, 3H): H$_d$ 4.03 ppm (singlet, 3H): H$_a$ 4.40 ppm (singlet, 2H): H$_b$ 5.30 ppm (singlet, 1H): H$_c$ 7.27–7.40 ppm (unresolved complex, 4H): H$_{2,3,6,8}$ 7.78–7.84 ppm (unresolved complex, 2H): H$_{4,5}$

EXAMPLE 2

N-Methyl-3-(7-Methoxy-1-Naphthyl)Propionamide

Example 2

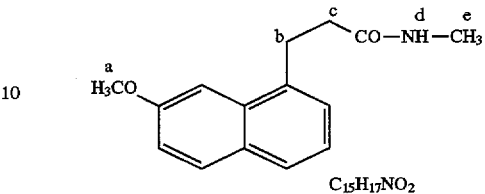

$C_{15}H_{17}NO_2$

Reagents:

3-(7-methoxy-1-naphthyl)propanoic acid: 0.3 g ($1.3 \times 10^{-3}$ mol)

$SOCl_2$ (118.97, d=1.631): 2.86 cm$^3$ ($2 \times 1.95 \times 10^{-2}$ mol)

40% aqueous methylamine (31.06, d=0.902): 0.34 cm$^3$ ($3.9 \times 10^{-3}$ mol)

Procedure:

0.3 g of 3-(7-methoxy-1-naphthyl)propanoic acid: is introduced into a 100 cm$^3$ flask and $SOCl_2$ is added, with stirring. The mixture is kept stirring for 1 h. The excess $SOCl_2$ is evaporated, cyclohexane is added and the mixture is kept stirring for 30 min. It is filtered and the filtrate is evaporated. The methylamine is added all at once. The mixture is kept stirring for 1 h. The aqueous phase is extracted with $3 \times 20$ cm$^3$ of toluene. The organic phase is washed with $3 \times 10$cm$^3$ of 10% $K_2CO_3$ and then with $3 \times 10$ cm$^3$ of 1N HCl and washed with water. It is dried over $CaCl_2$ and evaporated under reduced pressure. The solid obtained is recrystallized.

Characteristics:

Molar mass: 243.31 g.mol$^{-1}$ for $C_{15}H_{17}NO_2$

Melting point: 98°–100° C.

Rf: 0.27

Eluent: ATC (4/4/2)

Yield: 78%

Recrystallization solvent: cyclohexane

Infrared spectroscopy analysis:

3060–3280 cm$^{-1}$: νNH amide

2880–2980 cm$^{-1}$: νCH alkyls 1630 cm$^{-1}$: νC═O amide 1590 cm$^{-1}$: νC═C aromatic 1250 cm$^{-1}$: νOCH$_3$ NMR spectroscopy analysis (300 MHz, CDCl$_3$, δ):

2.60 ppm (triplet, 2H): H$_c$ J$_{b-c}$=7.68 Hz 2.75 ppm (doublet, 3H): H$_e$ J$_{c-d}$=4.77 Hz 3.40 ppm (triplet, 2H): H$_b$ J$_{b-c}$=7.68 Hz 3.95 ppm (singlet, 3H): H$_a$ 5.30 ppm (singlet, 1H): broad peak, NH 7.13–7.35 ppm (unresolved complex, 4H): H$_{2,3,6,8}$ 7.62 ppm (doublet, 1H): H$_4$ J ortho=7.49 Hz 7.79 ppm (doublet, 2H): H$_5$ J ortho=8.89 Hz.

EXAMPLE 3

N-Methyl 4-(7-Methoxy-1-Naphthyl)Butyramide

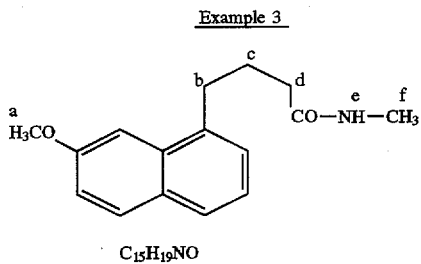

Example 3

$C_{15}H_{19}NO$

Reagents:

4-(7-methoxy-1-naphthyl)butyric acid: 1 g ($4.1 \times 10^{-3}$ mol)

$NH_2CH_3$: 6.36 ($82 \times 10^{-3}$ mol)

$SOCl_2$ (118.97d=1.631): 3 cm³ ($41 \times 10^{-3}$ mol)

Anhydrous cyclohexane: 30 cm³

Procedure:

The acid is introduced into a 50 cm³ round-bottomed flask, $SOCl_2$ is added and the mixture is kept stirring for 45 minutes. 20 cm³ of cyclohexane are added and the medium is kept stirring for 30 minutes and then filtered and evaporated to dryness. The residue is taken up in 10 cm³ of cyclohexane and $NH_2CH_3$ is added all at once. The medium is kept stirring until it is cooled and then the white precipitate formed is filtered. The residue is recrystallized.

Characteristics:

Molar mass: 257.33 g.mol⁻¹ for $C_{16}H_{15}NO_2$

Melting point: 96°–98° C.

Rf: 0.33

Eluent: ATC (4/4/2)

Yield: 93%

Recrystallization solvent: cyclohexane (then water/alcohol)

Infrared spectroscopy analysis:

3300 cm⁻¹: νNH amide

2980–2800 cm⁻¹: νCH 1630 cm⁻¹: νCO amide 1590 cm⁻¹: νC=C 1250 cm⁻¹: νOCH₃

NMR spectroscopy analysis (300 MHz, CDCl₃, δ):

2.05 ppm (multiplet, 2H): $H_c$ 2.30 ppm (triplet, 2H): $H_d$ $J_{d-c}$=7.58 Hz 2.80 ppm (doublet, 3H): $H_f$ $J_{f-e}$=3.89 Hz 3.51 ppm (triplet, 2H): $H_b$ $J_{b-c}$=7.68 Hz 4.03 ppm (singlet, 3H): $H_a$ 5.61 ppm (signal, 1H): $H_e$, exchangeable in $D_2O$ 7.23–7.35 ppm (unresolved complex, 1H): $H_{2,3,6,8}$ 7.66 ppm (doublet, 1H): $H_4$ $J_{ortho}$=7.91 Hz 7.78 ppm (doublet, 1H): $H_5$ $J_{ortho}$=9.00 Hz

EXAMPLE 4

N-Propyl-4-(7-Methoxy-1-Naphthyl)Butyramide

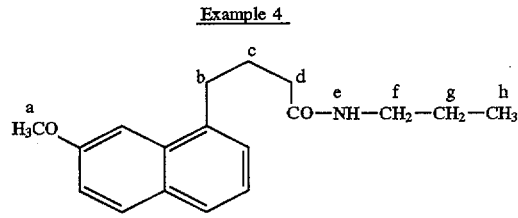

Example 4

Reagents:

4-(7-methoxy-1-naphthyl)butyric acid: 1 g ($4.1 \times 10^{-3}$ mol)

$SOCl_2$: 3 cm³ ($41 \times 10^{-3}$ mol)

$NH_2C_3H_7$: 6.74 cm³ ($8.2 \times 10^{-3}$ mol)

Procedure:

By carrying out the procedure as in Example 3, but replacing the methylamine with propylamine, the title compound is obtained.

Characteristics:

Molar mass: 285.39 g.mol⁻¹ for $C_{18}H_{23}NO_2$

Melting point: 109°–112° C.

Rf: 0.51

Eluent: ATC (4/4/2)

Yield: 38%

Recrystallization solvent: water/alcohol (2/1) (then cyclohexane)

Infrared spectroscopy analysis:

3300–3040 cm⁻¹: νNH amide

2940–2820 cm⁻¹: νCH alkyl 1630 cm⁻¹: νCO amide 1610 and 1590 cm⁻: νC=C aromatic 1260 cm⁻¹: νOCH₃

NMR spectroscopy analysis (300 MHz, CDCl₃, δ):

0.91 ppm (triplet, 3H): $H_h$ $J_{h-g}$=7.41 Hz 1.50 ppm (multiplet, 2H): $H_g$ 2.05 ppm (multiplet, 2H): $H_c$ 2.27 ppm (triplet, 2H): $H_d$ $J_{d-c}$=7.63 Hz 3.20 ppm (triplet, 2H): $H_f$ $J_{f-g}$=7.19 Hz 3.50 ppm (triplet, 2H): $H_b$ $J_{b-c}$=7.71 Hz 4.02 ppm (singlet, 3H): $H_a$ 5.61 ppm (signal; 1H): $H_e$, exchangeable in $D_2O$ 7.23–7.35 ppm (unresolved complex, 4H): $H_{2,3,6,8}$ 7.67 ppm (split doublet, 1H): $H_4$ $J_{ortho}$=7.99 Hz, $J_{meta}$=1.35 Hz 7.77 ppm (doublet, 1H): $H_5$ $J_{ortho}$=8.99 Hz

EXAMPLES 5 TO 15

By carrying out the procedure as in Example 1, but using the appropriate amine, the title compounds are obtained:

EXAMPLE 5
N-Ethyl-2-(7-Methoxy-1-Naphthyl)Acetamide

EXAMPLE 6
N-Propyl-2-(7-Methoxy-1-Naphthyl)Acetamide

EXAMPLE 7
N-Butyl-2-(7-Methoxy-1-Naphthyl)Acetamide

EXAMPLE 8
N-Pentyl-2-(7-Methoxy-1-Naphthyl)Acetamide

EXAMPLE 9
N-HEXYL-2-(7-Methoxy-1-Naphthyl)Acetamide

EXAMPLE 10
N-Isopropyl-2-(7-Methoxy-1-Naphthyl)Acetamide

EXAMPLE 11
N-Isobutyl-2-(7-Methoxy-1-Naphthyl)Acetamide

EXAMPLE 12
N-(Cyclopropylmethyl)-2-(7-Methoxy-1-Naphthyl)Acetamide

EXAMPLE 13
N-(Cyclobutyl)-2-(7-Methoxy-1-Naphthyl)Acetamide

EXAMPLE 14
N-(Cyclohexyl)-2-(7-Methoxy-1-Naphthyl)Acetamide

EXAMPLE 15
N-Allyl-2-(7-Methoxy-1-Naphthyl) Acetamide

EXAMPLES 16 TO 26

By carrying out the procedure as in Example 2, but using the appropriate amine, the title compounds are obtained:

EXAMPLE 16
N-Ethyl-3-(7-Methoxy-1-Naphthyl)Propionamide

EXAMPLE 17
N-Propyl-3-(7-Methoxy-1-Naphthyl)Propionamide

EXAMPLE 18
N-Butyl-3-(7-Methoxy-1-Naphthyl)Propionamide

EXAMPLE 19
N-Pentyl-3-(7-Methoxy-1-Naphthyl)Propionamide

EXAMPLE 20
N-Hexyl-3-(7-Methoxy-1-Naphthyl)Propionamide

EXAMPLE 21
N-Isopropyl-3-(7-Methoxy-1-Naphthyl)Propionamide

EXAMPLE 22
N-Isobutyl-3-(7-Methoxy-1-Naphthyl)Propionamide

EXAMPLE 23
N-(Cyclopropylmethyl)-3-(7-Methoxy-1-Naphthyl)Propionamide

EXAMPLE 24
N-(Cyclobutyl)-3-(7-Methoxy-1-Naphthyl)Propionamide

EXAMPLE 25
N-(Cyclohexyl)-3-(7-Methoxy-1-Naphthyl)Propionamide

EXAMPLE 26
N-Allyl-3-(7-Methoxy-1-Naphthyl)Propionamide

EXAMPLES 27 TO 36

By carrying out the procedure as in Example 3, but using the appropriate amine, the title compounds are obtained:

EXAMPLE 27
N-Ethyl-4-(7-Methoxy-1-Naphthyl)Butyramide

Melting point:: 123°–128° C.

EXAMPLE 28
N-Butyl-4-(7-Methoxy-1-Naphthyl)Butyramide

EXAMPLE 29
N-pentyl-4-(7-Methoxy-1-Naphthyl)Butyramide

EXAMPLE 30
N-Hexyl-4-(7-Methoxy-1-Naphthyl)Butyramide

EXAMPLE 31
N-Isopropyl-4-(7-Methoxy-1-Naphthyl)Butyramide

EXAMPLE 32
N-Isobutyl-4-(7-Methoxy-1-Naphthyl)Butyramide

EXAMPLE 33
N-(Cyclopropylmethyl)-4-(7-Methoxy-1-Naphthyl)Butyramide

EXAMPLE 34
N-(Cyclobutyl)-4-(7-Methoxy-1-Naphthyl)Butyramide

EXAMPLE 35
N-(Cyclohexyl)-4-(7-Methoxy-1-Naphthyl)Butyramide

EXAMPLE 36
N-Allyl-4-(7-Methoxy-1-Naphthyl)Butyramide

EXAMPLES 37 TO 47

By carrying out the procedure as in Example 1, but using preparations 3 to 13, the compounds of the following examples are obtained:

EXAMPLE 37
N-Methyl 4-(5-Fluoro-3-Indolyl)Butyramide

EXAMPLE 38
N-Methyl 3-(5-Methyl-3-Benzothiophenyl)Propionamide

EXAMPLE 39
N-Methyl 3-(5-Benzyloxy-3-Benzothiophenyl)Propionamide

EXAMPLE 40
N-Methyl 3-(5-Propyl-3-Indolyl)Propionamide

EXAMPLE 41
N-Methyl 3-(5-Trifluoromethyl-3-Indolyl)Propionamide

EXAMPLE 42
N-Methyl 3-(6-Methoxy-3-Benzofuryl)Propionamide

EXAMPLE 43
N-Methyl 4-(5-Methoxy-3-Benzofuryl)Butyramide

EXAMPLE 44
N-Methyl 4-(6-Methoxy-3-Indolyl)Butyramide

EXAMPLE 45
N-Methyl 3-(5-Ethoxy-3-Indolyl)Propionamide

EXAMPLE 46
N-Methyl 4-(4,6-Dimethoxy-3-Indolyl)Butyramide

EXAMPLE 47
N-Methyl 3-(5-Hydroxy-3-Benzofuryl)Propionamide

EXAMPLES 48 TO 58

By carrying out the procedure as in the preceding examples, but using the appropriate reagents and raw materials, the compounds of the following examples are obtained:

EXAMPLE 48

N-Methyl 4-(7-Hydroxy-1-Naphthyl)Butyramide

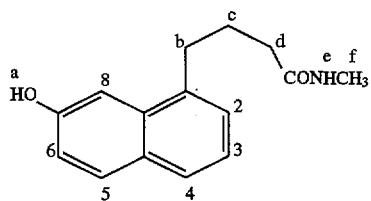

Reagents:

N-Methyl-4-(7-methoxy-1-naphthyl)butyramide (Example 3): 1 g ($3.9 \times 10^{-3}$ mol)

Boron tribromide: 1.12 cm$^3$ ($11.7 \times 10^{-3}$ mol)

Dichloromethane: 10 cm$^3$

Procedure:

The N-methyl-4-(7-methoxy-1-naphthyl)butyramide is dissolved in dichloromethane in a 100 cm$^3$ flask. The flask is placed in an ice bath at $-5°$ C. and the medium is allowed to cool, with stirring, for 20 minutes. The boron tribromide is added dropwise. After 15 minutes, the medium is hydrolyzed by pouring it over ice cold water. It is extracted with ethyl acetate. This phase is dried over MgSO$_4$ and evaporated. The oil is purified by silica gel chromatography.

Characteristics:

Molar mass: 243.31 g.mol$^{-1}$ for $C_{15}H_{17}NO_2$

Appearance: oil

Rf: 0.40

Eluent: ATC (4/4/2)

Yield: 99%

Purification: column chromatography with the eluent mentioned above

Infrared spectroscopy analysis:

3380–3080 cm$^{-1}$: νNH amide and OH phenol

2920–2840 cm$^{-1}$: νCH alkyls 1640 cm$^{-1}$: νCO amide 1610 and 1580 cm$^{-1}$: νC=C aromatic NMR spectroscopy analysis (80 MHz, CDCl$_3$, δ):

1.90–2.35 ppm (unresolved complex, 4H): H$_{c,d}$ 2.70 ppm (doublet, 3H): H$_f$ J$_{f-e}$=5.30 Hz 2.90 ppm (triplet, 2H): H$_b$ J$_{b-c}$=8.00 Hz 5.85 ppm (signal, 1H): H$_e$, exchangeable in D$_2$O 7.00–7.80 ppm (unresolved complex, 6H): H$_{2,3,4,5,6,8}$ (Ha not visible)

Elemental analysis:

Calculated: C: 74.05% H: 7.04% O: 13.15% N: 5.76%

Found: C: 74.10% H: 7.09% O: 13.09% N: 5.70%

EXAMPLE 49

N-Methyl 4-(7-Allyloxy-1-Naphthyl)Butyramide

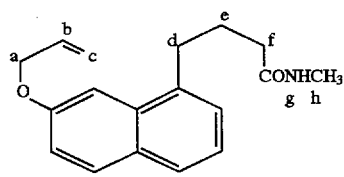

Reagents:

N-Methyl-4-(7-hydroxy-1-naphthyl)butyramide (Example 48): 2.15 g ($8.8 \times 10^{-3}$ mol)

Potassium carbonate: 3.66 g ($26.4 \times 10^{-3}$ mol)

Allyl bromide: 3.82 cm$^3$ ($44.0 \times 10^{-3}$ mol)

Anhydrous acetone: 20 cm$^3$

Procedure:

The naphtholic compound is dissolved in the anhydrous acetone. The potassium carbonate is added and the mixture is kept stirring under reflux for 30 minutes. The allyl bromide is then added dropwise. The mixture is kept under reflux and stirring for 3 h. After cooling, the reaction medium is filtered and the filtrate evaporated. The residue is recrystallized from a suitable solvent.

Characteristics:

Molar mass: 283.37 g.mol$^{-1}$ for $C_{18}H_{21}NO_2$

Appearance: white solid

Melting point: 119°–122° C.

Rf: 0.48

Eluent: ATC (4./4/2)

Yield: 60%

Recrystallization solvent: Toluene

Infrared spectroscopy analysis:

3240–3060 cm$^{-1}$: νNH amide

2920–2840 cm$^{-1}$: νCH alkyls 1630 cm$^{-1}$: νCO amide 1605 and 1580 cm$^{-1}$: νC=C aromatic 1245 cm$^{-1}$: νC—O aryl ether NMR spectroscopy analysis (300 MHz, CDCl$_3$, δ):

2.09 ppm (multiplet, 2H): H$_e$ 2.24 ppm (triplet, 2H): H$_f$ J$_{f-e}$=7.11 Hz 2.78 ppm (doublet, 3H): H$_h$ J$_{h-g}$=4.02 Hz 3.04 ppm (triplet, 2H): H$_d$ J$_{d-e}$=7.40 Hz 4.70 ppm (doublet, 2H): H$_a$ J$_{a-b}$=7.90 Hz 5.33 ppm (split doublet, 1H): H$_c$ J$_{c-b}$=10.50 Hz, J$_{c-c'}$=1.40 Hz 5.50 ppm (split doublet, 1H): H$_{c'}$ J$_{c'-b}$=17.30 Hz, J$_{c'-c}$=1.40 Hz 5.59 ppm (signal, 1H): H$_g$, exchangeable in D$_2$O 6.13 ppm (multiplet, 1H): H$_b$ 7.16–7.27 ppm (unresolved complex, 3H): H$_{2,3,6}$ 7.36 ppm (doublet, 1H): H$_8$ J$_{meta}$=2.28 Hz 7.64 ppm (split doublet, 1H): H$_4$ J$_{ortho}$=6.70 Hz, J$_{meta}$=2.64 Hz 7.75 ppm (doublet, 1H): H$_5$ J$_{ortho}$=8.95 Hz Elemental analysis:

Calculated: C: 76.30% H: 7.47% O: 11.29% N: 4.94%

Found: C: 76.59% H: 7.47% O: 11.31% N: 4.89%

EXAMPLE 50

N-Methyl-4-(8-Allyl-7-Hydroxy-1-Naphthyl) Butyramide

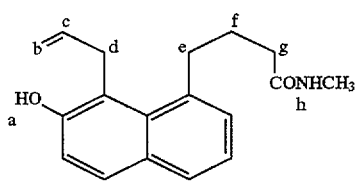

Reagents:
  N-Methyl-4-(7-allyloxy-1-naphthyl)-butyramide (Example 49): 1 g ($3.5\times10^{-3}$ mol)
  N,N-Dimethylaniline: 20 cm$^3$ Procedure:
The allyl ether is dissolved in the N,N-dimethylaniline and the reaction medium is heated at reflux (200° C.) for 2 h. After cooling, 50 cm$^3$ of ether are added and the organic phase is extracted with a 10% aqueous sodium hydroxide solution and then with water. The aqueous phase is then acidified with a 6N aqueous HCl solution and kept stirring for a few minutes. The precipitate formed is filtered and recrystallized from a suitable solvent.

Characteristics:
  Molar mass: 283.37 g.mol$^{-1}$ for $C_{18}H_{21}NO_2$
  Appearance: white solid
  Melting point: 131°–134° C.
  Rf: 0.38
  Eluent: ATC (4/4/2)
  Yield: 66%
  Recrystallization solvent: Toluene Infrared spectroscopy analysis:
  3380 cm$^{-1}$: νNH amide and phenolic OH
  2940–2840 cm$^{-1}$: νCH alkyls
  1630 cm$^{-1}$: νCO amide
  1605 and 1590 cm$^{-1}$: νC=C aromatic NMR spectroscopy analysis (300 MHz, DMSO d$_6$, δ):

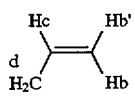

1.80 ppm (multiplet, 2H): H$_f$
  2.16 ppm (triplet, 2H): H$_g$ J$_{g\text{-}f}$=7.31 Hz
  2.58 ppm (doublet, 3H): H$_i$ J$_{i\text{-}h}$=3.67 Hz
  3.01 ppm (triplet, 2H): H$_e$ J$_{e\text{-}f}$=7.89 Hz
  3.83 ppm (doublet, 2H): H$_d$ J$_{d\text{-}c}$=4.57 Hz
  4.65 ppm (split doublet, 1H): H$_{b'}$ J$_{b'\text{-}c}$=17.28 Hz, J$_{b'\text{-}b}$=1.84 Hz
  4.93 ppm (split doublet, 1H): H$_b$ J$_{b\text{-}c}$=10.24 Hz, J$_{b\text{-}b'}$=1.84 Hz
  6.03 ppm (multiplet, 1H): H$_c$
  7.13–7.22 ppm (unresolved complex, 3H): H$_{2,3,6}$
  7.61–7.68 ppm (unresolved complex, 2H): H$_{4,5}$
  7.80 ppm (quadruplet, 1H): H$_h$ J$_{h\text{-}i}$=3,67 Hz
  9.57 ppm (signal, 1H): H$_a$, exchangeable in D$_2$O Elemental analysis:
  Calculated: C: 76.30% H: 7.47% O: 11.29% N: 4.94%
  Found: C: 76.48% H: 7.53% O: 11.25% N: 4.85%

EXAMPLE 51

N-Methyl-4-(8-Allyl-7-Methoxy-1-Naphthyl) Butyramide

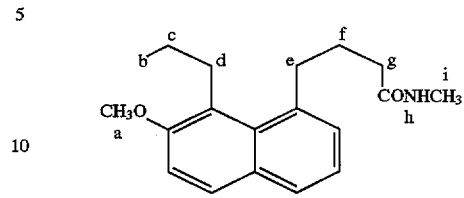

Reagents:
  N-Methyl-4-(8-allyl-7-hydroxy-1-naphthyl)butyramide (Example 50): 1 g ($3.5\times10^{-3}$ mol)
  Dimethyl sulfate: 3.35 cm$^3$ ($35.0\times10^{-3}$ mol)
  10% aqueous sodium hydroxide solution: 14 cm$^3$ ($35.0\times10^{-3}$ mol)

Procedure:
The N-methyl-4-(8-allyl-7-hydroxy-1-naphthyl)butyramide compound is dissolved in a 10% aqueous sodium hydroxide solution at 50° C. The heating is stopped after 30 minutes and the mixture is allowed to cool and then the dimethyl sulfate is added dropwise. The mixture is kept stirring for 30 minutes and the basic aqueous phase is extracted with 3 times 20 cm$^3$ of ether. The organic phase is washed with water until the washings become neutral. The organic phase is dried over MgSO$_4$, filtered and evaporated on a water bath under vacuum. The residue is recrystallized from a suitable solvent.

Characteristics:
  Molar mass: 297.40 g.mol$^{-1}$ for $C_{19}H_{23}NO_2$
  Appearance: white solid
  Melting point: 84°–86° C.
  Rf: 0.51
  Eluent: ATC (4/4/2)
  Yield: 68%
  Recrystallization solvent: Toluene-Cyclohexane (1-2)

Infrared spectroscopy analysis:
  3240 and 3060 cm$^{-1}$: νNH amide
  2980–2810 cm$^{-1}$: νCH alkyls
  1620 cm$^{-1}$: νCO amide
  1600 and 1580 cm$^{-1}$: νC=C aromatic
  1240 cm$^{-1}$: νOCH$_3$ aryl ether NMR spectroscopy analysis (300 MHz, CDCl$_3$, δ):

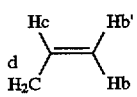

2.00 ppm (multiplet, 2H): H$_f$
  2.25 ppm (triplet, 2H): H$_g$ J$_{g\text{-}f}$=7.52 Hz
  2.78 ppm (doublet, 3H): H$_i$ J$_{i\text{-}h}$=4.59 Hz
  3.17 ppm (triplet, 2H): H$_e$ J$_{e\text{-}f}$=7.74 Hz
  3.92–3.96 ppm (unresolved complex, 5H): H$_{a,d}$
  4.72 ppm (split doublet, 1H): H$_{b'}$ J$_{b'\text{-}c}$=17.22 hz, J$_{b'\text{-}b}$=1.89 Hz
  5.00 ppm (split doublet, 1H): H$_b$ J$_{b\text{-}c}$=8.38 Hz, J$_{b\text{-}b'}$=1.89 Hz
  5.58 ppm (signal, 1H): H$_h$
  6.11 ppm (multiplet, 1H): H$_c$ 7.19–7.29 ppm (unresolved complex, 3H): $H_{2,3,6}$ 7.65 ppm (split doublet, 1H): $H_4$ $J_{ortho}=8.16$ Hz, $J_{meta}=1.67$ Hz 7.76 ppm (doublet, 1H): $H_5$ $J_{ortho}=8.98$ Hz Elemental analysis:

Calculated: C: 76.74% H: 7.80% O: 10.76% N: 4.71%

Found: C: 76.94% H: 7.99% O: 10.78% N: 4.72%

EXAMPLE 52

N-Methyl-4-(8-Allyl-7-Propoxy-1-Naphthyl)Butyramide

Example 52

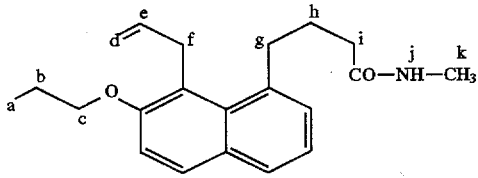

Reagents:

N-Methyl-4-(8-allyl-7-hydroxy-1-naphthyl)butyramide (Example 50): 0.94 g ($3.3 \times 10^{-3}$ mol)

Potassium carbonate: 1.37 g ($10.0 \times 10^{-3}$ mol)

1-Iodopropane: 1.63 $cm^3$ ($16.5 \times 10^{-3}$ mol)

Anhydrous acetone: 20 $cm^3$

Procedure:

The naphtholic compound is dissolved in the anhydrous acetone. The potassium carbonate is added and the mixture is kept stirring under reflux for 30 minutes. The iodopropane is added dropwise. The mixture is kept under reflux and stirring for 3 h. After cooling, the reaction medium is filtered and the filtrate is evaporated. The residue is recrystallized from a suitable solvent.

Characteristics:

Molar mass: 325.45 g.$mol^{-1}$ for $C_{21}H_{27}NO_2$

Appearance: white solid

Melting point: 69°–71° C.

Rf: 0.53

Eluent: ATC (4/4/2)

Yield: 82%

Recrystallization solvent: Cyclohexane

Infrared spectroscopy analysis:

3260 $cm^{-1}$: vNH amide

2940–2840 $cm^{-1}$: vCH alkyls

1625 $cm^{-1}$: vCO amide 1600 and 1590 $cm^{-1}$: vC=C aromatic

1250 $cm^{-1}$: vC=O aryl ether

NMR spectroscopy analysis (300 MHz, $CDCl_3$, δ):

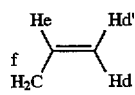

1.07 ppm (triplet, 3H): $H_a$ $J_{a-b}=7.42$ Hz 1.83 ppm (multiplet, 2H): $H_b$ 2.00 ppm (multiplet, 2H): $H_h$ 2.24 ppm (triplet, 2H): $H_i$ $J_{i-h}=7.50$ Hz 2.78 ppm (doublet, 3H): $H_k$ $J_{k-j}=4.58$ Hz 3.17 ppm (triplet, 2H): $H_g$ $J_{g-h}=7.72$ Hz 3.97 ppm (doublet, 2H): $H_f$ $J_{f-e}=4.88$ Hz 4.03 ppm (triplet, 2H): $H_c$ $J_{c-b}=6.43$ Hz 4.75 ppm (split doublet, 1H): $H_{d'}$ $J_{d'-e}=17.24$ Hz, $J_{d-d'}=1.81$ Hz 4.98 ppm (split doublet, 1H): $H_d$ $J_{d-e}=10.27$ Hz, $J_{d-d'}=1.81$ Hz 5.54 ppm (signal, 1H): $H_j$ 6.09 ppm (multiplet, 1H): $H_e$ 7.18–7.28 ppm (unresolved complex, 3H): $H_{2,3,6}$ 7.64 ppm (split doublet, 1H): $H_4$ $J_{ortho}=7.80$ Hz, $J_{meta}=1.35$ Hz 7.73 ppm (doublet, 1H): $H_5$ $J_{ortho}=8.97$ Hz Elemental analysis:

Calculated: C: 77.50% H: 8.36% O: 9.83% N: 4.30%

Found: C: 77.43% H: 8.27% O: 9.80% N: 4.20%

EXAMPLE 53

N-Methyl-4-(7-Propoxy-1-Naphthyl)Butyramide

Melting point: 102°–105° C.

EXAMPLE 54

N-Methyl-4-(2,3-Dihydro-3-Oxo-1-Naphtho[1,2-b]Furan)Butyramide

EXAMPLE 55

N-Methyl-4-(2,3-Dihydro-3-Hydroxy-1-Naphtho[1,2-b]Furan)Butyramide

EXAMPLE 56

N-Methyl-4-(1-Naphtho[1,2-b]Furan)Butyramide

EXAMPLE 57

N-Methyl-4-(2H-1-Naphtho[1,2-b]Pyran)Butyramide

EXAMPLE 58

N-Propyl4-(2,3-Dihydro-3-Oxo-1-Naphtho[1,2-b]Furan)Butyramide

EXAMPLE 59

N-Propyl-4-(2,3-Dihydro-3-Hydroxy-1-Naphtho[1,2-b]Furan)Butyramide

EXAMPLE 60

N-Propyl-4-(1-Naphtho[1,2-b]Furan)Butyramide

EXAMPLE 61

N-Propyl-4-(2H-1-Naphtho[1,2-b]Pyran)Butyramide

PHARMACOLOGICAL STUDY

EXAMPLE A

Study of Acute Toxicity

Acute toxicity was assessed after oral administration to batches of 8 mice (26±2 grams). The animals were observed at regular intervals during their first day and daily during the two weeks following the treatment. The $LD_{50}$, causing the death of 50% of the animals, was evaluated.

The $LD_{50}$ of the product tested is greater than 1 000 mg.kg$^{-1}$ for most of the compounds studied, which indicates the low toxicity of the compounds of the invention.

EXAMPLE B

Study of the Binding to the Melatonin Receptors

B1) Study on sheep pars tuberalis cells

The studies of binding of the compounds of the invention to the melatonin receptors were performed according to conventional techniques on sheep pars tuberalis cells. The pars tuberalis of the adenohypophysis is indeed characterized, in mammals, by a high density of melatonin receptors (Journal of Neuroendocrinology 1989, vol. (1), pp 1–4).

PROCEDURE

1) The sheep pars tuberalis membranes are prepared and used as target tissue in saturation experiments in order to determine the binding capacities and affinities for 2-[$^{125}$I] iodomelatonin.

2) The sheep pars tuberalis membranes are used as target tissue, with the various compounds to be tested, in competitive binding experiments compared with 2-iodomelatonin.

Each experiment is performed in triplicate and a range of different concentrations is tested for each compound.

The results make it possible to determine, after statistical treatment, the binding affinities of the compound tested.

RESULTS

It appears that the compounds of the invention possess a potent affinity for the melatonin receptors greater than that of melatonin itself.

B2) Study on chicken (*Gallus domesticus*) brain cell membranes

The animals used are 12-day old chickens (*Gallus domesticus*). They are sacrificed between 13 and 17 hours on the day of their arrival. The brains are rapidly removed and frozen at −200° C. and then stored at −80° C. The membranes are prepared according to the method described by Yuan and Pang (Journal of Endocrinology 1991, 128, pp 475–482). 2-[$^{125}$I]Iodomelatonin is incubated in the presence of membranes in a buffered solution at pH 7.4 for 60 min at 25° C. At the end of this period, the membrane suspension is filtered (Whatman GF/C). The radioactivity retained on the filter is determined with the aid of a Beckman® LS 6000 liquid scintillation counter.

The products used are:
2-[$^{125}$I]iodomelatonin
melatonin
common products
compounds tested In primary screening, the molecules are tested at 2 concentrations ($10^{-7}$ and $10^{-5}$M). Each result is the mean of n=3 independent measurements. The compounds tested are subjected to a quantitative determination of their efficacy ($IC_{50}$). They are used at 10 different concentrations.

Thus, the $IC_{50}$ values found for the preferred compounds of the invention, which correspond to the affinitive values, show that the binding of the compounds tested is very strong.

EXAMPLE C

Four-Plate Test

The products of the invention are administered via the esophageal route to batches of ten mice. One batch receives gum syrup. 30 min after administration of the products to be studied, the animals are placed in housings, the floor of which comprises four metal plates. Each time the animal passes from one plate to another, it receives a slight electric shock (0.35 mA). The number of passes is recorded for one minute. After administration, the compounds of the invention significantly increase the number of passes, showing the anxiolytic activity of the compounds of the invention.

EXAMPLE D

Compounds of the Invention on the Circadian Rhythms of Rat Locomotor Activity

The involvement of melatonin in driving, by day/night alternation, most physiological, biochemical and behavioral circadian rhythms made it possible to establish a pharmacological model for research for the melatoninergic ligands.

The effects of the molecules are tested on numerous parameters and, in particular, on the circadian rhythms of locomotor activity which represent a reliable marker for the activity of the endogenous circadian clock.

In this study, the effects of such molecules are evaluated on a specific experimental model, namely, rats placed in temporal isolation (permanent darkness).

EXPERIMENTAL PROCEDURE

One-month old Long Evans male rats are subjected, on their arrival at the laboratory, to a light cycle of 12 h of light per24 h (LD 12: 12).

After 2 to 3 weeks of adaptation, they are placed in cages equipped with a wheel linked to a recording system in order to detect the phases of locomotor activity and thereby to monitor the nychthemeral (LD) or circadian (DD) rhythms.

As soon as the recorded rhythms indicate a stable driving by the light cycle LD 12: 12, the rats are placed in permanent darkness (DD).

Two to three weeks later, when the free mode (rhythm reflecting that of the endogenous clock) is clearly established, the rats receive a daily administration of the molecule to be tested.

The observations are made by the visualization of the rhythms of activity:
driving of the rhythms of activity by means of the light rhythm,
disappearance of the driving of the rhythms in permanent darkness,
driving by the daily administration of the molecule; transient or lasting effect.

A software makes it possible:
to measure the duration and the intensity of the activity, the period of the rhythm in the animals in the free mode and during the treatment,
to demonstrate if appropriate, by spectral analysis, the existence of circadian and noncircadian components.

RESULTS

It appears clearly that the compounds of the invention make it possible to act strongly on the circadian rhythm via the melatoninergic system.

EXAMPLE E

Activity of the Products of the Invention on the Ischemic Microcirculation

The experimental study was performed on male rats (Sprague-Dawley) cremaster muscles after ligation of the common lilac artery.

The muscles were placed in a transparent chamber, perfused with a bicarbonate buffer solution equilibrated with a gaseous mixture $CO_2/N_2$ 5/95%. The velocity of the red blood cells and the diameter of the arteriols of the first or second order irrigating the cremaster were measured, the arteriolar blood flow was calculated. Identical information was obtained for four types of veinlets.

The same type of measurement is carried out simultaneously:
on the cremaster perfused normally,
on the cremaster under ligation, that is to say the cremaster ischemized 2, 7, 14 and 21 days after ligation.

Two groups of animals were studied:
a control group without treatment,
a group treated per os with a product of the invention, at the rate of 0.1 $mg.kg^{-1}$ per day.

No difference was observed in the velocity of the red blood cells or in the diameter of the vessels in the cremaster muscles normally irrigated in the treated animals compared with the control.

On the other hand, at the level of the ischemized cremaster muscle, the mean diameter of the arteriols was enhanced in the treated animals compared with the control. The velocity of the red blood cells was normalized by a treatment of 21 days.

In fact, in the treated animals, the velocity of the red blood cells and the blood flow rate measured 7 days after the ligation show no significant difference with the values obtained in the nonischemized cremaster. The results are obtained without modification of the blood pressure.

These results indicate that the chronic treatment with a compound of the invention enhances the microcirculation and the blood irrigation of the ischemized territories.

EXAMPLE F

Stimulation of the Immune Responses

Sheep red blood cells were administered to groups of six mice. These groups of mice were then treated subcutaneously with the compounds of the invention for six days and a control group was treated with a placebo. The mice are then allowed to rest for four weeks and then they received a booster injection of sheep red blood cells without receiving further administrations of product of the invention. The immune response was evaluated 3 days after the booster injection. It is statistically increased in the group treated with the compounds of the invention.

EXAMPLE G

Inhibition of Ovulation

Adult female rats with regular four-day cycles are used.

Daily vaginal smears were prepared and rats were selected after showing at least two consecutive four-day cycles.

Each cycle consists of two days of diestrus, one day of proestrus and one day of estrus.

On the afternoon of the day of proestrus, the luteinizing hormone is liberated in the blood by the hypophysis. This hormone induces ovulation which is manifested by the presence of eggs in the oviduct on the day of estrus. The compounds of the invention are administered orally at noon on the day of estrus. The treated and control female rats are sacrificed on the day of estrus. The oviducts are examined. A significant percentage of reduction in the number of eggs in the oviducts of treated female rats is observed.

EXAMPLE H

Antiarrhythmic Activity

PROCEDURE (ref: Lawson J. N. et al. J. Pharmacol. Exper. Therap. 1968, 160, pp 22–31)

The substance tested is administered intraperitoneally to a group of 3 mice 30 min before exposure to a chloroform anesthetic. The animals are then observed for 15 min. The absence of recording of arrhythmias and of heart rate greater than 200 beats/min (control: 400–480 beats/min) in the animals indicates a significant protection.

EXAMPLE I

Anti-Platelet Aggregation Activity

PROCEDURE (Ref.: Bertele V. et al. Science. 220: 517–519, 1983 Ibid, Eur. J. Pharmacol. 85: 331–333, 1982)

The compounds of the invention (100 µg/ml) are tested for their capacity to inhibit irreversible platelet aggregation induced by sodium arachidonate (50 µg/ml) in rabbit plasma enriched with platelets.

A more than 50% inhibition of the maximum aggregation indicates a significant activity for the compounds of the invention.

This in vitro test shows that the compounds of the invention are good candidates for the treatment of cardiovascular diseases, especially thromboses.

EXAMPLE J

Extension of the Bleeding Time

PROCEDURE (Ref.: Diana E. et al. Thrombosis Research. 15: 191–197, 1979)

Butler K. D. et al. Thromb. Haemostasis. 47: 46–49, 1982)

The compounds to be tested are administered orally (100 mg/kg) to a group of 5 mice 1 h before the standardized severing of the end of each tail (0.5 mm).

The mice are immediately suspended vertically, the tails being immersed over 2 cm in a test tube containing an isotonic saline solution at 37° C.

The time required for the bleeding to stop for a period of 15 seconds is then determined.

A more than 50% extension of the bleeding time relative to a control group of animals is considered to be significant for the compounds of the invention.

This in vivo test confirms the benefits of the compounds of the invention for the treatment of cardiovascular pathologies since the compounds of the invention extend the bleeding time.

EXAMPLE K

Hypobaric Hypoxia Test

PROCEDURE (Ref.: Gotti B., and Depoortere H., Circ. Cerebrale, Congrès de Circulation Cérébrale, Toulouse, 105–107, 1979)

The compounds to be tested are administered intraperitoneally (100 mg/kg) to a group of 3 mice 30 minutes before being placed in a chamber at a hypobaric pressure of 20 cmHg.

The extension of the survival time by more than 100% compared with a group of animals treated with the vehicle in the absence of a depressant effect of the central nervous system indicates a cerebroprotective activity of the compounds of the invention.

EXAMPLE L

Pharmaceutical Composition: Tablets 1000 tablets containing 5 mg doses of N-methyl-4-(7-methoxy-1-naphthyl)butyramide

| N-methyl-4-(7-methoxy-1-naphthyl)butyramide | 5 g |
| Wheat starch | 20 g |
| Corn starch | 20 g |
| Lactose | 30 g |
| Magnesium stearate | 2 g |
| Silica | 1 g |
| Hydroxypropyl cellulose | 2 g |

We claim:

1. A compound selected from the group consisting of those of formula (I):

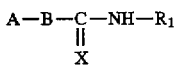  (I)

in which:

A represents a group of formula:

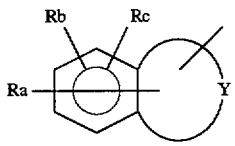

in which:

Y forms with the benzo nucleus carrying it a ring selected from the group consisting of naphthalene, dihydronaphthalene, tetrahydronaphthalene, benzofuran, 2,3-dihydrobenzofuran, benzothiophene, 2,3-dihydrobenzothiophene, indole, indoline, 2H-indene, and indan;

Ra, Rb, and Rc, each independently of each other, represent a hydrogen atom or a radical selected from the group consisting of halogen, hydroxy, —Rd and —O—Rd; with Rd being selected from the group consisting of alkyl, alkyl substituted with halogen, alkenyl, alkynyl, cycloalkyl, cycloalkylalkyl, aryl, arylalkyl, substituted aryl, and substituted arylalkyl;

it also being possible for Ra to form with Rb and the 2 adjacent carbon atoms carrying them a ring $A_1$ selected from the group consisting of furan, dihydrofuran, pyran, and dihydropyran, $A_1$ being optionally substituted by one or more radicals or groups selected from the group consisting of hydroxy, alkyl, alkoxy, and oxo;

B represents an alkylene chain having 2 to 6 carbon atoms, inclusive unsubstituted or substituted with a radical selected from the group consisting of alkyl, alkoxy, hydroxy, carboxy, alkoxycarbonyl, carboxyalkyl, and alkoxycarbonylalkyl, it being understood that B may also represent methylene when Y forms with the benzo nucleus carrying it naphthalene, dihydronaphthalene, or tetrahydronaphthalene, and that Ra, Rb, and Rc do not simultaneously represent hydrogen;

with the proviso that Ra, Rb, and Rc cannot simultaneously represent hydrogen or one hydrogen and 2 methyl or 2 hydrogen atoms and one methyl when Y forms, with the benzo nucleus to which it is attached, indole, and that the compound of formula (I) cannot be N-methyl-3-(4-methoxy-1-naphthyl)propionamide or N-tert-butyl-3-carboxy-4-(1-naphthyl)butyramide, X represents an oxygen or a sulfur atom;

and $R_1$ represents a radical selected from the group consisting of alkyl, alkyl substituted with halogen, alkenyl, alkynyl, cycloalkyl, and cycloalkylalkyl, it being understood that:

the terms "alkyl" and "alkoxy" designate linear or branched groups containing 1 to 6 carbon atoms, inclusive, the terms "alkenyl" and "alkynyl" designate linear or branched unsaturated groups containing 2 to 6 carbon atoms, inclusive the term "cycloalkyl" designates a group having 3 to 8 carbon atoms, the term "aryl" designates a phenyl, naphthyl, or pyridyl radical, the term "substituted" applied to the expressions "aryl" and "arylalkyl" means that these groups may be substituted with one or more radicals selected from the group consisting of halogen, alkyl, alkoxy, hydroxy and alkyl substituted with halogen; inclusive its enantiomers and diastereoisomers, and an addition salt thereof with a pharmaceutically-acceptable acid or base.

2. A compound of claim 1, which is N-methyl-2-(7-methoxy-1-naphthyl)acetamide.

3. A compound of claim 1, which is N-methyl-3-(7-methoxy-1-naphthyl)propionamide.

4. A compound of claim 1, which is N-propyl-4-(7-methoxy-1-naphthyl)butyramide.

5. A compound of claim 1, wich is N-methyl-4-(7-hydroxy-1-naphthyl)butyramide.

6. A compound of claim 1, wich is N-methyl-4-(7-allyloxy-1-naphthyl)butyramide.

7. A compound of claim 1, wich is N-methyl-4-(8-allyl-7-hydroxy-1-naphthyl)butyramide.

8. A pharmaceutical composition containing a compound of claim 1 in combination with one or more pharmaceutically-acceptable excipients.

9. A method of treating a mammal afflicted with a disorder of the melatoninergic system comprising the step of administering to the said mammal an amount of a compound of claim 1 which is effective to alleviate the said disorder.

10. A method of treating a mammal afflicted with a sleep disorder comprising the step of administering to the said mammal an amount of a compound of claim 1 which is effective to alleviate the said disorder.

* * * * *

UNITED STATES PATENT AND TRADEMARK OFFICE
CERTIFICATE OF CORRECTION

PATENT NO. : 5,721,276
DATED : February 24, 1998
INVENTOR(S) : I. Lesieur; P. Depreux; V. Leclerc; P. Delagrange; P. Renard; B. Lemaitre It is certified that error appears in the above-indentified patent and that said Letters Patent is hereby corrected as shown below:

Column 8, line 35: In the formula (I/m), "B-C(=O)-NH-R₁" should read -- B-C(X)-NH-R₁ --.

Column 19, line 53: " Methoxy -/- " should read -- Methoxy -1- --.

Column 31, line 63: Insert a -- , -- (comma) after the word "inclusive".

Column 32, line 29: Insert the word -- inclusive -- at the end of the line after "atoms,".

Column 32, line 36: Delete the word "inclusive" at the end of the line after "halogen;".

Signed and Sealed this

Third Day of April, 2001

Attest:

Attesting Officer

NICHOLAS P. GODICI

Acting Director of the United States Patent and Trademark Office